US00PP18056P2

(12) United States Plant Patent
Jonkers et al.

(10) Patent No.: US PP18,056 P2
(45) Date of Patent: Sep. 18, 2007

(54) ***IMPATIENS* PLANT NAMED 'SILTE PINKA'**

(50) Latin Name: *Impatiens walleriana*
Varietal Denomination: Silte Pinka

(75) Inventors: Johanna B. Jonkers, Andijk (NL); Erik Smit, Enkhuizen (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 11/410,385

(22) Filed: Apr. 25, 2006

(51) Int. Cl.
*A01H 5/00* (2006.01)

(52) U.S. Cl. ..... Plt./317
(58) Field of Classification Search ..... Plt./317
See application file for complete search history.

*Primary Examiner*—Kent Bell
(74) *Attorney, Agent, or Firm*—Jondle & Associates, P.C.

(57) ABSTRACT

A new *Impatiens* plant particularly distinguished by large, double, pink, rose-shaped flowers borne well-above the foliage, deep-green foliage with elliptical leaves, an early flowering response, floriferous throughout the summer and a medium, round and bushy plant habit, is disclosed.

1 Drawing Sheet

Genus and species: *Impatiens walleriana.*
Variety denomination: 'Silte Pinka'.

BACKGROUND OF THE NEW PLANT

The present invention comprises a new and distinct cultivar of *Impatiens,* botanically known as *Impatiens walleriana,* and hereinafter referred to by the cultivar name 'Silte Pinka'. The new cultivar originated from a hybridization made in April 2003 in Andijk, The Netherlands. The female parent was the proprietary deep-pink-flowered *Impatiens* plant 'IDY-14-9' (unpatented), while the male parent was the proprietary salmon-flowered *Impatiens* plant 'IDY-29-2' (unpatented). The seeds produced by the hybridization were sown in Andijk, The Netherlands in July 2003. A single plant selection was chosen for further evaluation and for asexual propagation in October 2003 in Andijk, The Netherlands.

The new cultivar was created in 2003 in Andijk, The Netherlands, and has been asexually reproduced repeatedly by vegetative cuttings and tissue culture in Andijk, The Netherlands and Hillscheid, Germany over a two-year period. 'Silte Pinka' has not been observed under all possible environmental conditions. The present invention has been found to retain its distinctive characteristics through successive asexual propagations.

Plant Breeder's Rights for this cultivar were applied for in Canada on Oct. 17, 2005 and with the European Union on Nov. 18, 2005.

SUMMARY OF THE INVENTION

The following are the most outstanding and distinguishing characteristics of this new cultivar when grown under normal horticultural practices in Andijk, The Netherlands, and Hillscheid, Germany.

1. Large, double, pink, rose-shaped flowers borne well-above the foliage;
2. Deep green foliage with elliptical leaves;
3. A round and bushy plant habit of medium height;
4. An early flowering response; and
5. Floriferous throughout the summer.

DESCRIPTION OF PHOTOGRAPH

This new *Impatiens* plant is illustrated by the accompanying photograph which shows overall plant habit including blooms, buds, and foliage of the plant; the colors shown are as true as can be reasonably obtained by conventional photographic procedures. The photograph is of a whole plant about 10- weeks old, grown in a greenhouse in Hillscheid, Germany in late May 2005.

DESCRIPTION OF THE NEW CULTIVAR

The following detailed descriptions set forth the distinctive characteristics of 'Silte Pinka'. The data which defines these characteristics were collected from asexual reproductions carried out in Hillscheid, Germany. The plant history was taken in mid September on 9- to 10-week old un-pinched plants which had been planted as rooted cuttings in 12-cm pots in mid-July 2005 and grown in a greenhouse at a minimum temperature of 21° C. Color readings were taken under natural light in the greenhouse. Color references are primarily to The R.H.S. Colour Chart of The Royal Horticultural Society of London (R.H.S.) (2001).

DETAILED BOTANICAL DESCRIPTION OF THE NEW PLANT

Classification:
- *Family.*—Balsaminaceae.
- *Botanical.*—*Impatiens walleriana* Hook.
- *Common name.*—*Impatiens.*

Parentage:
- *Female parent.*—'IDY-14-9' a proprietary deep-pink-flowered *Impatiens* plant (unpatented).
- *Male parent.*—'IDY-29-2' a proprietary salmon-flowered *Impatiens* plant (unpatented).

Growth:
- *Growth and branching habit.*—A medium-sized plant and when un-pinched, has a fairly upright growth habit with few basal, but many secondary branches; pinching of the terminal apices leads to more basal branching, more spreading and a more evenly mounding plant habit.

*Height.*—19.8 cm.
*Width.*—13.0 cm.
*Propagation.*—Terminal tips for cuttings.
*Time to produce a finished flowering plant.*—8 weeks for a 12-cm pot.
*Time to initiate and develop roots.*—18 days or less at 22° C.

Branches:
*Average number.*—6.0.
*Length of main branches.*—16 cm to 18 cm.
*Internode length.*—0.5 cm.
*Diameter of branches* (*at midpoint*).—0.7 cm to 0.8 cm.
*Stem color.*—RHS 144B to RHS 146D (light green).

Leaves:
*Arrangement.*—Mainly alternate.
*Size.*—Length: 11.0 cm. Width: 4.2 cm.
*Shape.*—Elliptical.
*Apex.*—Acuminate.
*Base.*—Acute.
*Margin.*—Weakly crenate, ciliated (sparse).
*Color* (*mature leaves*).—Deep green. Upper surface: RHS 137A. Lower surface: RHS 138B.
*Color* (*immature leaves*).—Upper surface: RHS 137A. Lower surface: RHS 138B and 185D, marbled.
*Texture.*—Dull, glabrous.
*Venation color.*—Upper surface: Indistinct Lower surface: RHS 144A near the base and RHS 146C for the upper portion.
*Petioles.*—Length: 2.5 cm to 3.5 cm. Diameter: 0.4 cm. Color: Upper surface: RHS 181D (weakly reddish). Lower surface: RHS 145D (pale-green). Texture: Glabrous.

Flower buds:
*Shape.*—Ovoid to nearly round.
*Size.*—Length: 1.4 cm. Diameter: 1.2 cm.
*Color at tight bud.*—RHS 73C.

Inflorescence:
*Blooming habit.*—6 to 8 weeks after planting of rooted cuttings.
*Inflorescence type.*—Peduncles bearing 2 to 4 flowers at different stages of development emerge from the leaf axils of the upper nodes of the stems.
*Flowering season.*—Continuously flowers, mainly from March to October, depending on light intensity.
*Lastingness of the individual blooms on the plant.*—About 5 to 7 days (at 18° C. in a greenhouse in the spring).
*Peduncle.*—Color: RHS 146D or RHS 147C. Size: Length: 7.5 cm. Diameter: 0.15 cm to 0.3 cm. Texture: Flexible, glabrous.

Flowers:
*Form of corolla.*—Double-type.
*Shape of corolla.*—Nearly round, rose-like.
*Corolla size.*—Diameter: 4.0 cm to 4.4 cm. Depth: About 2.0 cm.
*Number of petals.*—More than 20.

Petals:
*Shape.*—Mostly obovate; banner petal is cordate.
*Apex.*—Rounded; banner petal is emarginate.
*Base.*—Attenuate.
*Margin.*—Entire.
*Petal size.*—Length: 1.8 cm to 2.2 cm. Width: 1.7 cm to 1.8 cm. Banner petal width: 2.2 cm.
*Color.*—Upper surface: RHS N66C or RHS 68A, most often with an RHS 53A (dark red) macule at the petal base (usually not visible) and with a fine RHS 53C (reddish) middle line. Lower surface: RHS 69B (pale pink).
*Texture.*—Smooth.
*Aspect.*—Outer petals are nearly horizontal or parallel to the surface of the foliage canopy.

Spur:
*Shape.*—Curved, downward directed.
*Color.*—Mainly RHS 146D (green) and RHS 49D at the tip.
*Size.*—Length: 2.6 cm. Diameter: 0.2 cm near the flower base.

Reproductive organs:
*Stamens.*—Not observed.
*Pistil.*—Style and stigma: Not developed. Ovary: 5-celled. Ovary length: 0.6 cm. Ovary color: RHS 143A (green).

Fruit and seed set: No seed set observed.

Disease and insect resistance: No particular resistance or susceptibility has been observed.

COMPARISON WITH PARENTAL AND COMMERCIAL CULTIVARS

'Silte Pinka' differs from the female parent 'IDY-14-9' (unpatented) by having pink, double flowers, while 'IDY-14-9' has deep-pink, single flowers.

'Silte Pinka' differs from the male parent 'IDY-29-2' (unpatented), by having pink, double flowers, while 'IDY-29-2' has salmon, single flowers.

'Silte Pinka' differs from the commercial cultivar 'Didi Pink' (U.S. Plant Pat. No. 11,532) by having smaller leaves, a freer branching and a lower, more evenly rounded plant habit than 'Didi Pink'.

I claim:

1. A new and distinct cultivar of *Impatiens* plant as shown and described herein.

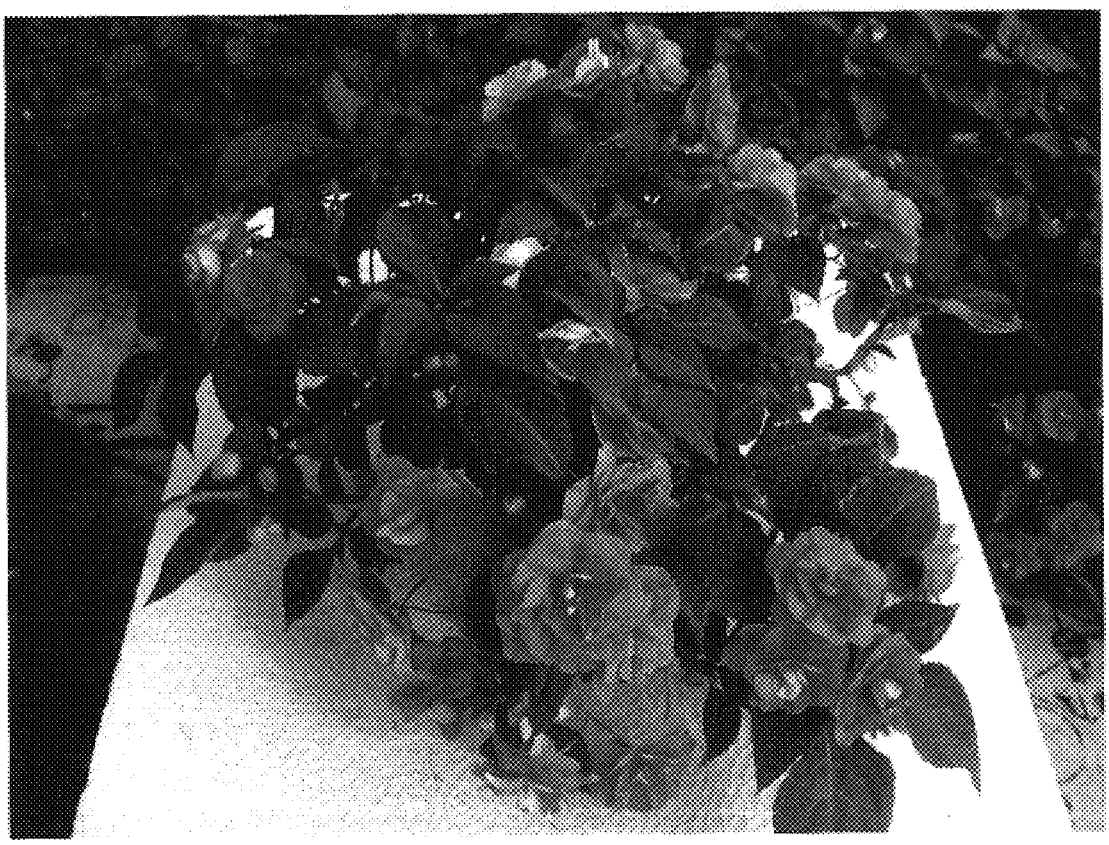

* * * * *